US00PP08331P

United States Patent [19]

Ilsink

[11] Patent Number: Plant 8,331

[45] Date of Patent: Aug. 3, 1993

[54] MINIATURE ROSE PLANT NAMED INTERHENK

[75] Inventor: G. P. Ilsink, Leersum, Netherlands

[73] Assignee: Interplant B.V., Leersum, Netherlands

[21] Appl. No.: 781,571

[22] Filed: Oct. 23, 1991

[51] Int. Cl.[5] ..... A01H 5/00

[52] U.S. Cl. ..... Plt./8.1

[58] Field of Search ..... Plt. 3, 7.1, 8.1, 8.2

*Primary Examiner*—Howard J. Locker

*Attorney, Agent, or Firm*—Christie, Parker & Hale

[57] ABSTRACT

A new variety of miniature rose plant having white flowers produced on a good pot forcing plant also suitable for growing outdoors in gardens.

2 Drawing Sheets

SUMMARY OF THE INVENTION

The present invention relates to a new and distinct variety of rose plant of the miniature rose class, which was originated by me by crossing as the seed and pollen parents unnamed and unpatented seedlings of my creation. The varietal denomination of the new variety is 'Interhenk'.

Among the novel characteristics possessed by this new variety which distinguishes it from its parent and all other varieties of which I am aware is its white flowers borne on a plant particularly suited for production of flowering pot plants and for growing in outdoor gardens. 'Interhenk' can be reproduced through propagation by cuttings, grafting and budding. Flowers of the new variety are long lasting on the plant. Asexual reproduction by budding, grafting, and propagation of cuttings of the new variety as performed in Hazerswoude, Holland, shows that the foregoing and other distinguishing characteristics come true to form and are established and transmitted through succeeding propagation.

BRIEF DESCRIPTION OF ILLUSTRATIONS

The accompanying illustrations show typical specimens of the vegetative growth and flowers of the new variety in different stages of development depicted in color as nearly true as it is reasonably possible to make the same in a color illustration of this character. Colors may vary depending upon growing conditions under different climate, soil, and cultivation conditions.

FIG. 1 is an illustration of a plant of the new variety of miniature rose showing flowering and growth habit; and FIG. 2 is an illustration showing details of the new miniature rose variety.

DETAILED DESCRIPTION OF THE NEW VARIETY

The following is a detailed description of my new variety, with color terminology in accordance with The Royal Horticultural Society Colour Chart (R.H.S.C.C.) and horticultural terminology in accordance with standard terminology used in UPOV-approved horticultural guidelines. The terminology used in color descriptions herein refers to plate numbers in the aforementioned color chart.

Parentage: Seedling.

*Seed parent.*—Unnamed seedling.

*Pollen parent.*—Unnamed seedling.

Class: Miniature.

Figure 1:
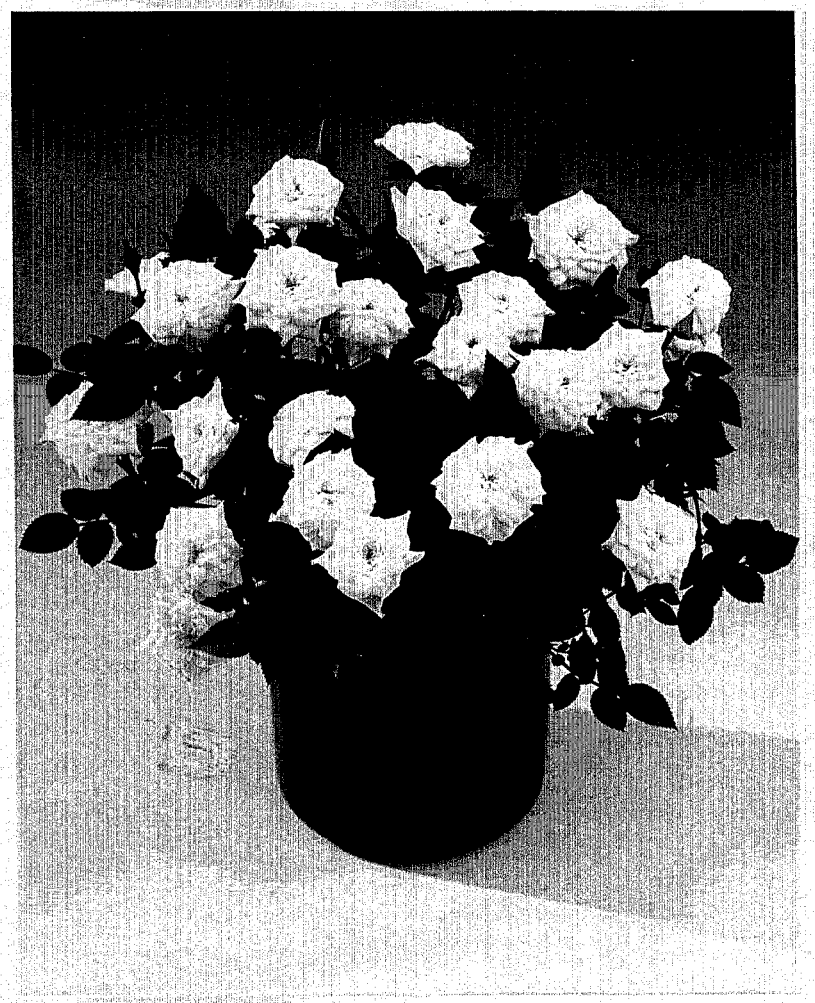

As can be seen in the accompanying illustrations, FIG. 1 shows one sample of flowering plant of 'Interhenk' depicting the pot plant habit of growth and flowering. Since flowering is nearly continuous, the floriferous 'Interhenk' can remain attractively in bloom for long periods when given proper care and culture.

Figure 2:
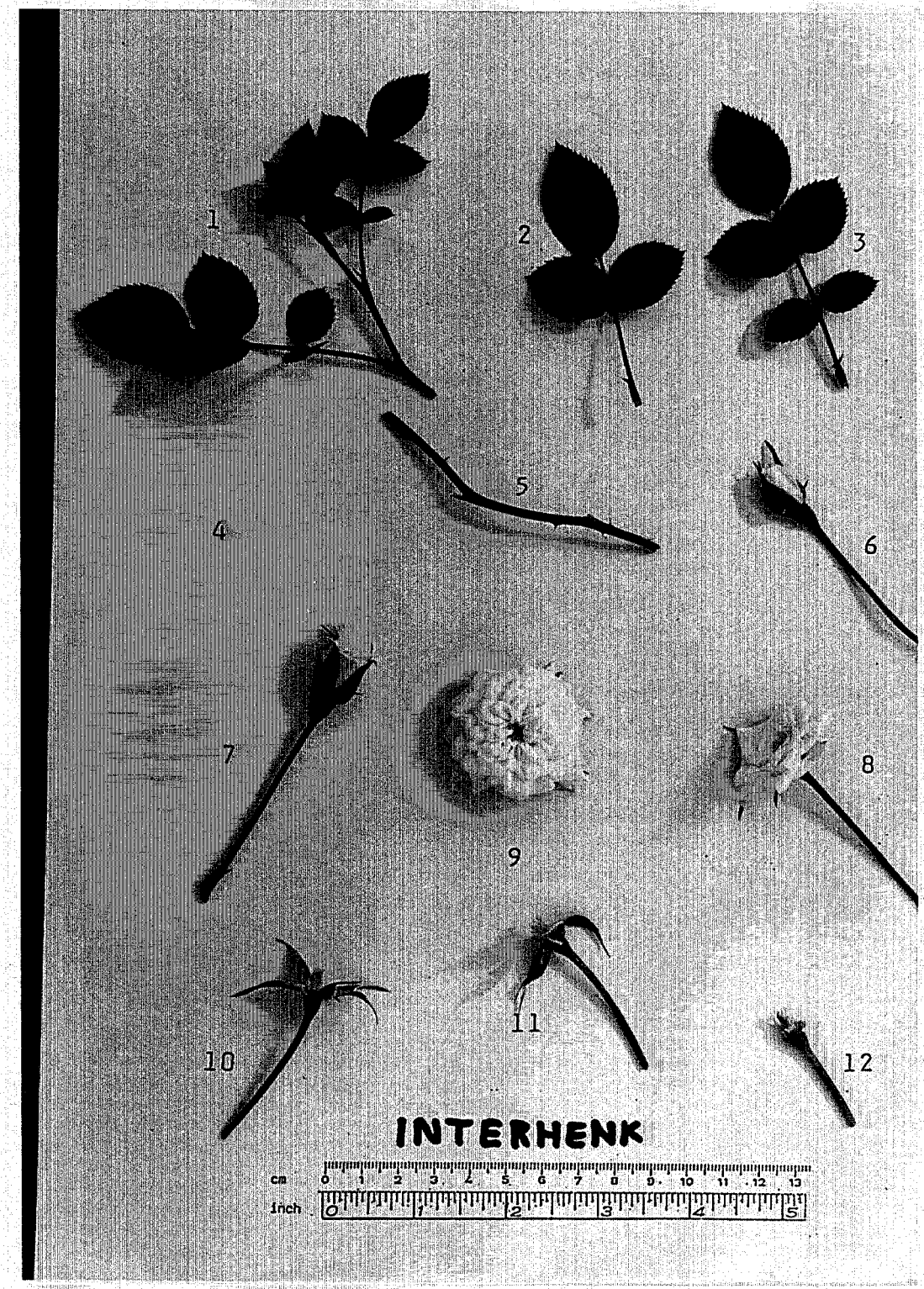

The illustration in FIG. 2 shows details of the new variety 'Interhenk'. In the illustration there is shown the top of a young shoot, 1; compound three and five leaflet leaves, 2 and 3, respectively; a stem, 5; buds, 6 and 7; a flower, 8, about one-half open; and a flower 9, fully open. Also shown are flower stems 10, 11 and 12, with reproductive organs.

The following further horticultural observations were made of specimens grown outdoors in Holland.

FLOWER

Blooming habit: Nearly continuous.

A. Bud:

(1) *Size.*—Medium.

(2) *Form.*—Pointed, ovate (before separation of sepals); urn shaped after sepals part.

(3) *Color.*—As sepals divide, bud color is near 11C-D to ivory.

(4) *Sepals.*—Longer than bud, simple to slightly foliated near 146A-B.

(5) *Peduncle.*—Length — about 5 to 6 cm. Aspect — straight. Strength — erect. Color — medium green.

B. Bloom:

(1) *Flower.*—Average size for miniature; viewed from above — star shaped to round; viewed from side — (a) upper part of fully opened flower — flattened convex; (b) lower part of fully opened flower — flat.

(2) *Size.*—Average size when fully expanded — about 4 to 5 cm.

(3) *Borne.*—Singly, one to a stem.

(4) *Form.*—Ovoid to cupped at first, becoming flat; outer petals reflex and quill to points; inner petals reflex and roll under slightly.

(5) *Petalage.*—Many petaled under normal conditions — fully double, average number of petals in a mature bloom is approximately 60.

(6) *Color.*—After sepals separate, near 155A to ivory; when sepals part and petals begin to unfurl, color is near 155A; petals top surface tends to near 155A, reverse sides tend to ivory at outer petals, near white on inner petals. Open flowers have non-white centers when reproductive organs show through. Coloring at point of petal attachment is near 6D. Overall tonality from a distance is almost pure white.

(7) *Pedicel.*—Medium number of hairs or prickles.

(8) *Fragrance.*—Slight to none.

C. Petals:

(1) *Texture.*—Medium.

(2) *Appearance.*—Inside velvety and outside satiny.

(3) *Form and size.*—Small, obovate.

(4) *Arrangement.*—Regularly arranged, imbricated.

(5) *Petaloids in center.*—Several.

(6) *Persistence.*—Drop off cleanly.

(7) *Lasting quality.*—Long lasting quality on plant, approximately 10–14 days.

REPRODUCTIVE ORGANS

A. Stamens, filaments and anthers:

*Arrangement and color.*—Regularly arranged around styles; color filaments yellow to yellow green but only sporadically present.

B. Pollen:

*Color.*—Yellow orange.

C. Styles: Long, stigma well above mouth of receptacle, yellow green, generally not hairy.

D. Stigmas: Positioned above anthers.

E. Hips: Small, pitcher-shaped.

PLANT

A. Form: Bushy.

B. Growth: Vigorous, average plant height attained is approximately 20 cm.

C. Foliage: Compound 3, and 5 leaflets.

(1) *Size.*—Medium for a miniature.

(2) *Quantity.*—Abundant.

(3) *Color.*—Foliage at time of first flowering — near 139A.

(4) *Shape.*—Oval, pointed.

(5) *Texture.*—Upper side is weakly glossy; underside is matte.

(6) *Edge.*—Serrate.

(7) *Serration.*—Ordinary, acuminate apices.

(8) *Leaf stem.*—Color — medium green.

(9) *Stipules.*—Short, simple, medium to light green, distinct auricle.

(10) *Leaflets.*—Cross section — flat, little or no undulation at margin; terminal leaflet — short to very short, narrow, rounded base; petiole — short.

D. Wood:

(1) *New wood.*—Color — medium green, young shoots have weak anthocyanin coloration — bronze.

(2) *Old wood.*—Color — near 146A-D.

E. Prickles (thorns):

(1) *Prickles.*—Present, quantity (main stalk) — ordinary; On laterals from stalk — ordinary; Form — straight; Shape of upper side — concave; Shape of lower side — concave; Length — $\leqq 5$ mm medium; $>5$ mm few; Color — tan to pale pink; Position — irregular.

F. Winter hardiness: Needs protection outdoors in severe climates.

G. Disease resistance: Average.

I claim:

1. A new and distinct variety of rose plant of the miniature rose class, substantially as shown and described.

* * * * *

UNITED STATES PATENT AND TRADEMARK OFFICE

CERTIFICATE OF CORRECTION

PATENT NO. : Plant 8,331

DATED : August 3, 1993

INVENTOR(S) : G.P. Ilsink

It is certified that error appears in the above-indentified patent and that said Letters Patent is hereby corrected as shown below:

Column 1, lines 1,11, in column 1, move the column heading "1" on line 11 to occur before "SUMMARY OF THE INVENTION".

Column 2, lines 1,1, in column 2 move the column heading "2" on (unnumbered) line 1 to occur before "*Pollen parent*.--Unnamed seedling."

Signed and Sealed this

Twenty-first Day of June, 1994

*Attest:*

Bruce Lehman

BRUCE LEHMAN

*Attesting Officer*

*Commissioner of Patents and Trademarks*